United States Patent [19]

Alagy et al.

[11] 4,126,638

[45] Nov. 21, 1978

[54] PROCESS FOR PURIFYING BENZENE DICARBOXYLIC ACIDS

[75] Inventors: Jacques Alagy, Lyons; Christian Busson, Rueil Malmaison; Maurice Cessou, Communay, all of France

[73] Assignee: Institut Francais du Petrole, France

[21] Appl. No.: 676,714

[22] Filed: Apr. 14, 1976

[30] Foreign Application Priority Data

Apr. 14, 1975 [FR] France ................ 75 11750

[51] Int. Cl.² ............................................ C07C 51/42
[52] U.S. Cl. ............................. 562/487; 562/416
[58] Field of Search ................................. 260/525

[56] References Cited

U.S. PATENT DOCUMENTS

| | | | |
|---|---|---|---|
| 2,840,604 | 6/1958 | Feighner et al. | 260/525 |
| 3,020,312 | 2/1962 | Moscrip | 260/525 |
| 3,456,001 | 7/1969 | Olsen | 260/525 |
| 3,584,039 | 6/1971 | Meyer | 260/525 |
| 3,637,831 | 1/1972 | Remsberg | 260/525 |

*Primary Examiner*—A. Siegel
*Attorney, Agent, or Firm*—Millen & White

[57] ABSTRACT

A benzene dicarboxylic acid is purified by heating a solution thereof to 110° – 350° C in the presence of a hydrogenation catalyst; the solvent is a mixture of water with a secondary or tertiary alcohol.

14 Claims, No Drawings

PROCESS FOR PURIFYING BENZENE DICARBOXYLIC ACIDS

The invention concerns the purification of benzene polycarboxylic acids, for example, isophthalic, orthophthalic and terephthalic acids.

The higher polyesters of polycarboxylic acids with various glycols have important applications as fibers, and it is absolutely necessary to employ very pure acids for the esterification.

A particularly important acid is terephthalic acid whose higher polyesters may be prepared by transesterification of methyl terephthalate with an appropriate glycol and polycondensation, with a view toward manufacturing a superpolyester. The manufacture of the polyester from methyl terephthalate is the essential step since the polyester must be of an exceptional purity.

It is thus necessary that terephthalic acid, from which methyl terephthalate is prepared, be very pure; otherwise the resulting polyester would have too low a melting point and undesirable shade.

The impurities of terephthalic acid are of two types: first, 4-carboxybenzaldehyde which is formed when preparing terephthalic acid by oxidation of a dialkylbenzene such as paraxylene and has a detrimental effect on the quality of the polyester; second, colored compounds such as fluorenones or benzylic compounds. The processes for the purification of terephthalic acid must allow a thorough removal of impurities of these types.

Various processes have been proposed, particularly for reducing the 4-carboxybenzaldehyde content.

The impurities of terephthalic acid and the other benzene polyacids cannot be removed by distillation, which would result in the decomposition of the desired acid, or by recrystallization, since the impurities are insoluble in most of the conventional solvents.

According to a known process, the impurities of the benzene polycarboxylic acids may be removed by hydrogenating these acids in aqueous solution, in the presence of a hydrogenation catalyst at a temperature of from about 200° to 400° C. This process, although yielding satisfactory results, is not really practical in view of the necessity of handling hydrogen and using it frequently at a relatively high partial pressure in order to permit dissolution and diffusion of the gas in the liquid phase, and it is also necessary to ensure a regular bubbling or agitation for the hydrogen dispersion and intimate contact of hydrogen with the solution.

According to another process for removing impurities from benzene polycarboxylic acids, these acids are treated in the absence of hydrogen, at a temperature of from 100° to 300° C., in the presence of a hydrogenation catalyst, the acid to be purified being dissolved in water or possibly in another solvent such as a ketone, an aliphatic acid or an amide. The use of an alcohol as solvent was absolutely prohibited since it is known, that the alcohols are not inert with respect to the acids, such as, in the present case the acid to be purified; they lead, under the experimental conditions of the purification, to the formation of esters and, sometimes, resins.

It has now been found that, according to this invention, far better purification rates can be obtained than according to the process of the prior art, while using an alcohol as solvent, provided this alcohol is not a primary alcohol and is admixed with water in a well-determined critical amount.

The process of the invention is conducted at 110°–350° C., in the absence of molecular hydrogen, in the presence of a hydrogenation catalyst, at a sufficient pressure to maintain a liquid reaction phase. According to the invention, the solvent is a mixture of water with an alcohol comprising from 0.5 to 50% by weight of alcohol, preferably 1 to 30%, particularly 1 to 7% and more preferably 1.5 to 3.5%, the remainder being water. It is thus possible, by the present process, to reduce the 4-carboxybenzaldehyde content to less than 10 parts by weight per million of parts of benzene polycarboxylic acid, without noticeable esterification of the acid to be purified.

Any secondary or tertiary water-soluble alcohol preferably containing 3 to 8 carbon atoms per molecule may be used. Non-limitative examples are: cyclopentanol, cyclohexanol, isopropanol, isobutanol, tertiobutanol, etc. Isopropanol is preferably used. Primary alcohols are not convenient.

The catalyst in the present invention is a conventional hydrogenation catalyst. It contains at least one noble metal of the platinum family deposited on a carrier at a concentration of from about 0.01 to 10% b.w. of the catalyst. The metal is thus platinum, palladium, ruthenium, rhodium, iridium or osmium. Two or more metals may be used, at the same or at different concentrations, the concentration of each metal being in the range of from 0.01 to 10% b.w. of the catalyst. Various carriers may be utilized for the metal (s) to be used, for example, active carbon, various aluminas, such as calcined alumina, preferably of high specific surface (for example higher than 30 m$^2$ per gram) and other inorganic oxides such as silicas, silica gel, titanium oxides, zirconias, magnesias, thorium and boron oxides, kieselguhr, bleaching earth, etc. Instead of depositing noble metals of the platinum family on the above carriers, other metals may be used, such as iron, cobalt, nickel, in finely divided form or as salts, such as the nitrates. Raney nickel, platinum or palladium black, nickel metal on kieselguhr are also convenient. The catalyst may be used as a more or less fine powder, in the form of granulates or conglomerates, etc.

The catalyst amount depends on its activity and the desired purification rate. As a rule, a highly pure acid may be obtained with only 20 to 800 ppm of metal by weight of acid to be treated, these values being not limitative. The optimal catalyst concentration may be easily determined, in accordance with the operating conditions and the purity of the acid to be purified. The acid treatment may be carried out with a fixed, fluid or moving bed of catalyst, continuously or batchwise.

The treatment time depends on the initial purity of the acid to be purified, and also on the final purity desired after purification. Thus the time of contact between the solution and the catalyst may range, for example, from a few minutes to a few hours.

After the treatment, according to the invention, the purified acid is recovered by any known means. For example, the solution may be separated from the catalyst and then cooled to crystallize the acid, the latter is separated from the mother-liquor by any known means and, if necessary, washed with an adequate solvent. The acid to be purified may be from any source.

Thus, for example, the impure terephthalic acid to which the process of the invention is applied may result from the oxidation of paraxylene in the liquid phase, either with air by using a heavy metal and bromine as catalyst, or with nitric acid.

The following non-limitative examples illustrate the invention. In each example, the 4-carboxybenzaldehyde content has been determined by dissolving the acid with a dilute alkali compound, the pH being brought to 9 by means of a buffer, and 4-carboxybenzaldehyde analyzed by polarography. The color, expressed in "T.E.G. color" units (triethylene glycol color), is determined by esterifying 4.0 g of the purified acid with 28.4 cc of triethylene glycol at 200° C., and then comparing the color of the resulting solution with reference samples of the American Public Health Association (A.P.H.A.)

EXAMPLE 1

TABLE I

| EXPERIMENT | A | B | C | D | E | F | G | H | I | J | K |
|---|---|---|---|---|---|---|---|---|---|---|---|
| % isopropanol b.w. (the remainder is water) | 0 | 0.5 | 1 | 2 | 3 | 4 | 6 | 10 | 35 | 55 | 100 |
| Resulting terephthalic acid 4-carboxybenzaldehyde content in ppm. | 12 | 9 | 8 | 3 | 4 | 5 | 8 | 9 | 11 | 5500 | 5500 |
| benzoic acid content in ppm. | 57 | <20 | <10 | <10 | <10 | <10 | <10 | <10 | <10 | Esters of terephthalic acid have formed | Esters of terephthalic acid have formed; partial resinification. |
| paratoluic acid content in ppm. | 195 | 86 | 46 | 38 | 40 | 41 | 43 | 59 | 100 | | |
| Color T.E.G. APHA | 12 | 9 | 5 | 4 | 5 | 5 | 6 | 7 | 12 | | |
| Optical density at 340 mμ | 0.108 | 0.084 | 0.019 | 0.018 | 0.019 | 0.020 | 0.026 | 0.048 | 0.092 | | |

No purification is possible ⇐

No purification is possible ⇐

The terephthalic acid sample to be purified has been obtained by oxidation of paraxylene with air, in the presence of bromhydric acid and cobalt acetate tetrahydrate. The reaction solvent was acetic acid. The obtained terephthalic acid contained 5,500 ppm by weight of 4-carboxybenzaldehyde. The T.E.G. color of this impure terephthalic acid was 240 and its optical density 1.09 at 340 mμ.

The conditions of the purification were as follows:
Temperature: 250° C.
Pressure: 40 kg/cm² in gauge
Space velocity (kg/hour/liter of solution): 0.550

The catalyst was consisting of 0.5% by weight palladium on a granular coal carrier. 3.8 kg of this sieved wet catalyst were introduced into a titanium pipe of 10 cm internal diameter. The length of the catalyst bed was 110 cm. The catalyst was arranged on a perforated titanium plate, the holes having a diameter of 1.05 mm and the centers of the holes being spaced by 2 mm. A solution of impure terephthalic acid was percolated through the column: the impure solution was supplied to the top of the column; the treated solution was discharged from the bottom of the column.

The so treated solution was collected under pressure, cooled and then depressurized. Terephthalic acid crystallized; it was recovered by filtration, then washed and dried. The solution, passed through the purification column at 250° C., contained about 7.5 g of impure terephthalic acid for 100 g of solvent.

The following table I indicates the 4-carboxybenzaldehyde content of the purified terephthalic acid in ppm, its T.E.G. color and optical density.

In experiment A, the solvent was pure water.

In experiments B–J, the solvent consisted of various mixtures of water with isopropanol.

In experiment K, the solvent was pure isopropanol.

EXAMPLE 2

According to experiments L, M and N of table II, the solvent was a mixture of 98% b.w. water with 2% of an alcohol, respectively cyclopentanol, cyclohexanol and 2-butanol. The other conditions were the same as in example 1.

By way of comparison, when using a mixture of 98% b.w. water with 2% b.w. ethanol (a primary alcohol) as solvent, the purification is unsatisfactory since ethanol tends to form esters with terephthalic acid.

TABLE II

| EXPERIMENT resulting terephthalic acid | L with 2% CYCLOPENTANOL (b.w.) | M with 2% CYCLOHEXANOL (b.w.) | N with 2% 2-BUTANOL (b.w.) |
|---|---|---|---|
| 4-carboxybenzaldehyde content in ppm | 5 | 6 | 6 |
| benzoic acid content in ppm | <10 | <10 | <10 |
| paratoluic acid content in ppm | 42 | 43 | 42 |
| Colour T.E.G. APHA | 6 | 6 | 7 |
| optical density at 340 mμ | 0.021 | 0.025 | 0.024 |

What we claim:

1. In a process for purifying terephthalic acid containing 4-carboxybenzaldehyde as an impurity, wherein said acid is dissolved in a solvent and treated at a temperature of from 110° to 350° C., at a pressure sufficient to maintain a liquid phase, in the presence of a hydrogenation catalyst and in the absence of molecular hydrogen, the improvement wherein the solvent is a mixture of water with a secondary or tertiary hydrocarbyl alcohol of 3 to 8 atoms, the mixture containing 0.5 to 7% by weight of said alcohol dissolved therein.

2. A process according to claim 1, wherein said mixture contains 1.5 to 3.5% by weight of alcohol.

3. A process according to claim 1, wherein said mixture contains 1 to 7% by weight of alcohol.

4. A process according to claim 1, wherein the terephthalic acid is derived from the liquid phase oxidation of paraxylene with molecular oxygen.

5. A process according to claim 1 wherein the alcohol is isopropanol.

6. A process according to claim 5, wherein the mixture comprises 1.5–3.5% by weight of alcohol.

7. A process according to claim 3, wherein the alcohol is isopropanol.

8. A process according to claim 6, wherein the alcohol is isopropanol.

9. A process according to claim 8, wherein the 4-carboxybenzaldehyde content is reduced to less than 10 parts by weight per million parts of benzene polycarboxylic acid.

10. A processing according to claim 7, wherein the hydrogenation catalyst is a supported catalyst comprising about 0.01–10% by weight of a metal from the platinum family.

11. A process according to claim 2, wherein the alcohol is cyclopentanol, cyclohexanol, isopropanol, isobutanol, or tertiobutanol.

12. A process according to claim 1 wherein the alcohol is cyclopentanol.

13. A process according to claim 1 wherein the alcohol is cyclohexanol.

14. A process according to claim 1 wherein the alcohol is butanol-2.

* * * * *